United States Patent
Lundborg

(10) Patent No.: US 6,589,287 B2
(45) Date of Patent: Jul. 8, 2003

(54) ARTIFICIAL SENSIBILITY

(76) Inventor: Göran Lundborg, Björndyorps by, S-240 13 Genarp (SE)

( * ) Notice: Subject to any disclaimer, the term of this patent is extended or adjusted under 35 U.S.C. 154(b) by 0 days.

(21) Appl. No.: 09/975,429

(22) Filed: Oct. 11, 2001

(65) Prior Publication Data

US 2002/0082710 A1 Jun. 27, 2002

Related U.S. Application Data

(63) Continuation-in-part of application No. 09/423,121, filed as application No. PCT/SE98/00786 on Apr. 29, 1998, now abandoned.

(30) Foreign Application Priority Data

Apr. 29, 1997 (SE) ................................................ 9701595
Apr. 29, 1998 (WO) ................................ PCT/SE98/00786

(51) Int. Cl.⁷ ................................. A61F 2/54; A61F 2/70
(52) U.S. Cl. .......................................... 623/24; 73/172
(58) Field of Search .............................. 623/24, 63–65; 414/5; 73/172

(56) References Cited

U.S. PATENT DOCUMENTS 4,650,492 A    3/1987    Barkhordar et al. .......... 623/24
4,655,673 A    4/1987    Hawkes ..................... 414/5 X

FOREIGN PATENT DOCUMENTS

JP              8-294503 A    * 11/1996    ............ A61F/2/54

* cited by examiner

Primary Examiner—David H. Willse
(74) Attorney, Agent, or Firm—Fasth Law Offices; Rolf Fasth

(57) ABSTRACT

The artificial sensibility device has a left sensor applied to a left finger, a middle sensor applied to a middle finger and a right sensor applied to a right finger of a hand. The sensors are connected to an amplifier unit that is connected to a headphone unit with a left speaker and a right speaker. The left finger is moved against a surface to activate the left sensor to send a first activation signal to the amplifier unit that sends a first sound signal only to the left speaker but nothing to the right speaker so the user knows the left finger is moved. The right finger is moved against the surface so that the right sensor sends a second sound signal only to the right speaker but nothing to the left speaker.

7 Claims, 2 Drawing Sheets

| Sensor | Headphone Left | Right |
|--------|----------------|-------|
| 16 | 100% | 0% |
| 18 | 75 | 25 |
| 20 | 50 | 50 |
| 22 | 25 | 75 |
| 24 | 0 | 100 |
| | | |

FIG. 2

ARTIFICIAL SENSIBILITY

PRIOR APPLICATION

This is a continuation-in-part application of U.S. patent application Ser. No. 09/423,121 filed Oct. 29, 1999 (now abandoned), which claims priority from PCT/SE98/00786, filed Apr. 29, 1998; which claims priority from Swedish Patent Application No. 9701595-2, filed Apr. 29, 1997.

TECHNICAL FIELD

The present invention relates to a device for improved artificial sensibility.

BACKGROUND AND SUMMARY OF THE INVENTION

The human hand is a grip organ that is often characterized by good grip power as well as adequate capacity for fine motor precision movements. The hand is also a sense organ that has an extremely well developed sensory function. The sensibility of the hand includes not only the ability to feel, for example, pressure, touch, vibration, temperature changes but also the ability to perceive the form, surface and texture of objects that are touched without requiring the person to see the objects, so called stereognosis. The function of the hand is to a large extent dependent on the sensory feedback system that is accomplished by sensibility. A hand without sensibility is a hand that does not function well.

There are many situations where lack of sensibility constitutes a major hindrance for the hand function and where some kind of artificial sensibility would be of great importance. A number of such situations are reviewed below.

Following amputation injuries of a forearm or an upper arm level, the patient can have good use of an artificial hand, i.e., a hand prosthesis that can replace the amputated hand. Such a hand prosthesis can be fixed to the amputated stump by the use of a sleeve enclosing the remaining part of the forearm or by titanium fixtures, such as according to the Brånemark model, which are implanted into the remaining parts of the skeleton. The prosthesis can be of merely a cosmetic nature without any possibility of movement or of a functional type with the possibility of active voluntary motion. The latter case refers to muscle-controlled myoelectric prostheses. These prostheses are controlled by electric activity, released by matter of will, in the muscles that remain in the amputation stump. By using the surface electrodes in the sleeve enclosing the amputation stump, such impulses in the extensor or flexor muscles are recorded and transformed for control of a motor in the prosthesis which can open or close the prosthetic hand.

Myoelectric hand prostheses can be very useful but many patients use their prostheses only to a limited extent or not at all. The direct reason is often that the prostheses lack sensibility and the patients thus lack the feedback function in the system. Many patients are dependent on visual observation of every movement in the prosthesis in order for the vision sense to, to some extent, compensate for the lack of sensibility. A system which enables real sensibility in such hand prosthesis, would dramatically improve its function.

Severe transection or crunch injuries in the arm or hand include lesion of one or several nerve trunks. For instance, transection of one of the major nerve trunks on the volar part of the wrist, such as the median nerve, results in total sensory lose within the major part of the hand. Such an injury results in major disability since the hand functions are very much impaired due to the sensory lose. Following surgical repair of the nerve, new nerve fibers grow in the hand but because of disorientation of nerve fibers and incomplete innervation, the sensibility often remains impaired in the hand. Following injury of nerve trunks at the wrist level, it takes about six months before there is any useful sensory recovery in the hand. During these months, when there is a complete sensory loss of the hand, the patient has great difficulties in exercising the hand since there is no sensory feedback. A system for artificial sensibility during this period would to a large extent facilitate the post-operative training and thus lead to a more rapid rehabilitation.

There are a large number of neurological diseases that may result in impaired sensibility or total sensory loss in the hand. In polyneuropathies, there may be such a sensory impairment in many parts of the body including the arms and hands. Such a neuropathy may exist in, for example, diabetes, alcohol abuse or impaired kidney functions. Impaired sensibility, can be present also in multiple sclerosis and stroke impaired patients. In industrial societies, sensory impairment due to long-term use of handheld vibrating tools is a major problem. In a global perspective, leprosy or lepra is the most obvious example of how sensory impairment results not only in impaired hand function but also in injuries and infections which may lead to spontaneous amputations of fingers, toes and other body-parts.

In these situations, restitution of sensibility in the hand and other body-parts could lead to a major advantage in terms of improved function and could also help to prevent injuries to the body.

The description, given above, has primarily addressed problems related to the hand and the upper extremity. Also, lower extremity sensory loss may lead to major problems. In diabetes, sensory loss in the foot may lead to wounds, infection, necrosis and amputation. In amputation injuries, prostheses may be very useful but because of lack of sensibility in the prostheses their use may be limited.

Artificial sensibility enables lost or impaired sensibility to be replaced by an alternative system for sensory feedback. To achieve such sensibility, the following is required: 1) Detection of a sensory stimuli, e.g., pressure or vibration, 2) Processing and transmission of the signal resulting from such a stimuli; and 3) Sensory perception based on the transmitted signal.

Registration of a stimulus requires some type of a sensor. For example, pressure piezo-resistive membranes have been used in, for example, the grip members of industrial robots. Also, in experiments on humans, piezo-resistive membranes applied to the fingertips of hand prostheses or denervated hands have been used. A pressure, applied to such a membrane, initiates an electric signal which is proportional to the applied pressure.

The electric signal can be processed and used for application of electric or vibro-tactile proportional stimuli to intact sensible skin on a suitable area of the same extremity or at some other part of the body. This principle, however, has major drawbacks. For example, due to rapid adaptation of the skin to such a stimulus, the skin becomes less sensitive. In addition, such a principle gives an unnatural alternative stimulus which can not be used for identification of the surface or structure that is touched.

One object of the present invention is to create possibilities of feeling with the help of the hearing sense to replace vibrotactile sensory stimuli with acoustic stimuli. The invention creates possibilities to, by using the hearing sense, identify the character of the surface and texture which is touched and to thereby achieve a descriptive functional sensory perception. The invention is based on a new principle for artificial sensibility based on a sense substitution, i.e., the use of an alternative sense to replace a lost sense.

Various types of sense substitution exist in daily life. For example, a blind person can read in Braille with the fingertips so that the vision is replaced by sensibility. A deaf person can read the movements of the lips of the contrahent, so that the hearing sense is replaced by vision, and can also feel and utilize the vibrations in the larynx of the contrahent so that the hearing sense is replaced by the sensibility.

BRIEF DESCRIPTION OF THE DRAWINGS

FIG. 2 shows an example of the sound distribution between left and right speakers in the present invention.

DETAILED DESCRIPTION

Figure 1:
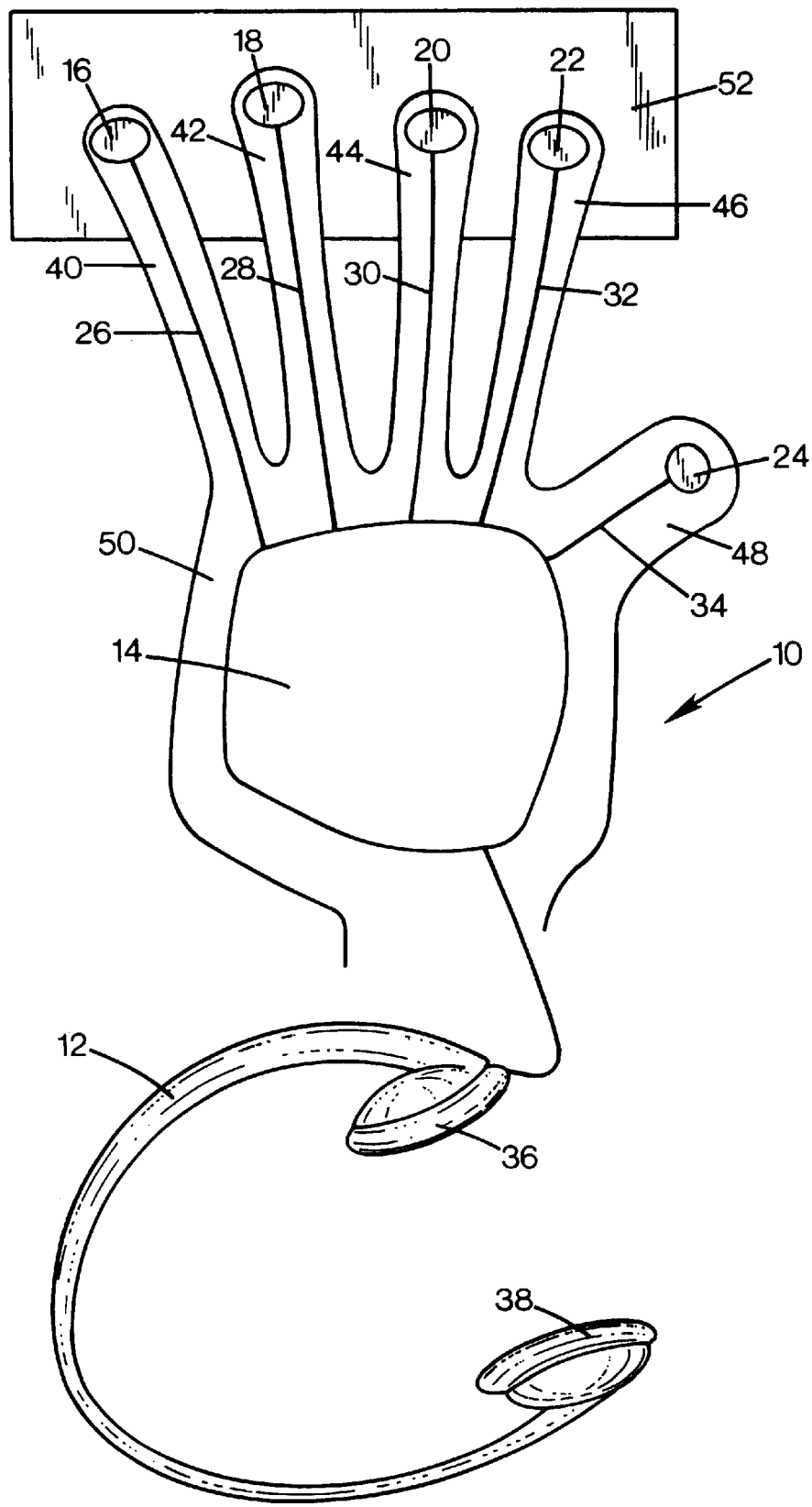
FIG. 1 shows an embodiment of the present invention.

In the prevailing invention, a lost sensibility is replaced by the hearing sense. The hearing sense is extremely well developed and mimics in that respect the sensory sense. The sensory sense, as well as the hearing sense, is to a great extent based on the detection and interpretation of vibration stimuli. The substitution of lost sensibility by hearing is therefore a biologically sound principle.

The principle is used which not only allows the registration and perception of changes in threshold levels, pressure, temperature etc, but also makes it possible to register and perceive the character of a surface and texture that is being touched to replace the descriptive, functional sensibility of the hand.

One main principle of the present invention is to replace absent or lost sensibility in a hand prosthesis, hand or other body-part with an alternate sense, the hearing sense, and to use the special qualities of the hearing sense to replace lost sensibility. When a hand normally touches a surface or an item, vibrations represented by a weak friction sound are always created. This friction sound is in each separate case very characteristic for the surface and texture which is touched. Normally this sound is very weak. In case of lost or absent sensibility, the present invention can, however, magnify and convert these friction sound stimuli to acoustic stimuli. The character of friction sound remains but the device of the present invention provides an increased perception of the friction sound that is generated when a surface is touched. Thus, the device of the present invention does not involve the use of falsified and un-psychological sound that may be characterized by tones.

If the signal is processed in a stereo amplifier and if both ears, alternatively bone conduction of both sides of the cranium, are utilized, the fingers of the hand can be projected in different spatial locations in space, like the sections of a symphony orchestra, which makes it possible for the patient to identify which finger or fingers do the touching. The principle can be combined with other systems for registration and perception of changes also with respect to, for example, touch and temperature.

The system requires a sensor system at the location of the surface that is being touched. The system also requires processing and amplifying equipment for stimulation of the hearing sense or the bone conduction system of the cranium of the patient.

In the present invention, the sensors are microphones or equivalent equipment of small dimensions which can register the friction sound generated when a surface or an item is touched, i.e., the vibrotactile stimulus. The friction sound is characteristic for the surface, texture and in some cases form and density of the item that is touched. The friction sound, which always can be heard faintly, is thus totally different when different materials are touched. In this way, metal, glass, rubber foam, linen, orange or apple surfaces produce different and distinct sound waves. In the hand prosthesis device, microphones can be incorporated directly in the fingers of the prosthesis. Regarding hands with lost and impaired sensibility, the sensor/sensors can be incorporated in a glove which can be applied to the damaged hand. The sensors can also be applied directly to nails and skin and can also be operated into the soft tissue of fingertips. In order to enable identification of separate fingers, it is of course important that the sensors are applied to multiple fingers.

The vibrotactile stimuli that are registered by the sensors when the hand or the prosthesis touches an object or slides over a surface is processed in an amplifying step which can be of stereophonic type. The signals are transmitted are possibly by wireless communication to earphones applied to one or both ears. The hearing phones can have very small dimensions. The signals can also be transmitted directly to the bone of the cranium by stimulators placed, for example, behind the external ears. Alternatively, the signals can be transmitted directly to the bone of the cranium by implants introduced into the bone.

With reference to FIG. 1, an embodiment of the device 10 of the present invention is shown. Preferably, the device 10 has stereophonic headphones 12 that are connected to an amplifier unit 14. The headphones 12 may be of any suitable type that has a left speaker 36 for the left ear of the user and a right speaker 38 for the right ear of the user.

The unit 14 may be connected to sensors 16, 18, 20, 22, 24 by, for example, wires 26, 28, 30, 32, 34. The sensors could be any suitable type of sensor including, but not limited to, microphones, temperature gauge and light sensors. The sensors 16–24 may be attached to upper sides of fingers 40, 42, 44, 46, 48 of a hand 50 of the user. The sensors may be attached to other body parts also such as the feet and arms. For example, the microphones may be focused on picking up vibrational sound from the finger tips when the finger tips touch or scratch a surface 52. The sensors may also be attached to the outside of a glove into which the hand 50 may be inserted. It should be understood that the sensors may communicate with the unit 14 via a wireless technology so that the wires 26–34 are not needed.

The device 10 may be designed so that vibrations that are sensed by the sensor 16 are only heard in the left speaker 36 and vibrations sensed by the sensor 24 are only heard in the right speaker 38. FIG. 2 shows an example of the sound distribution between the left and right speakers 36, 38 so that the sound created by any vibrational sound sensed and transmitted by the sensor 18 is heard 75% of the total sound volume in the left speaker 36 and 25% of the total sound volume in the right speaker 38. Similarly, any vibrational sound transmitted by the sensor 22 is heard 75% of the total in the right speaker 38 and 25% of the total in the left speaker 36. Any vibrational sound sensed and transmitted by the sensor 20 is evenly distributed between the left and right speakers 36, 38. Of course, the device 10 may be designed so that the sound is distributed according to different percentages as the above example. The amplifier unit 14 may be designed to distribute the sound signals according to a predetermined distribution and to amplify according to the requirements of the user. The signals from the sensors may also be displayed on a computer screen that may be used when the user is training to use the device 10.

The sensors 16, 18, 20, 22, 24 may produce sounds at different frequencies. For example, the frequency of the sound from the sensor 16 may be at a higher frequency compared to the frequency transmitted by the sensor 18. The frequency of the sound from the thumb 48 may be the lowest. In this way, the user may know from the frequency of the sound which finger is used.

The sensors may also be connected to certain parts of the brain so that when one sensor is activated a certain part of the brain is also activated and when another sensor is activated a different part of the brain is activated. For example, the sensors may be designed to send an alarm signal when the temperature at the finger or finger tip is above or below a certain temperature. In this way, the user knows to quickly remove the finger to avoid burning or frost bite damage of the finger. The device 10 may also be designed to send different signals depending upon the temperature so that the user knows which temperature interval the finger is exposed to.

In operation, the user may attached the device 10 to the hand 50. If the user has severe damage the nerve connections to one or many fingers, the user may use the device 10 to train to recognize the sound created when the damaged finger is moved relative to surfaces. For example, a smooth surface produces a different sound compared to a rough surface. One important feature of the present invention is that listening to the sound from different surfaces is more stimulating and speeds up the recovery compared to the merely seeing the nerve damaged finger touch a surface.

While the present invention has been described in accordance with preferred compositions and embodiments, it is to be understood that certain substitutions and alterations may be made thereto without departing from the spirit and scope of the following claims.

We claim:

1. A method of using an artificial sensibility device, comprising:

providing a device comprising a left sensor applied to a left finger, a middle sensor applied to a middle finger and a right sensor applied to a right finger of a hand, the sensors being connected to an amplifier unit, the amplifier unit being connected to a headphone unit having a left speaker and a right speaker;

moving the left finger against a surface to activate the left sensor, the left sensor sending a first activation signal to the amplifier unit;

the amplifier unit sending all of a first sound signal to the left speaker and no sound signal to the right speaker;

moving the right finger against the surface to activate the right sensor, the right sensor sending all of a second sound signal to the right speaker and no sound signal to the left speaker; and moving the middle finger against the surface to activate the middle sensor, the middle sensor sending a first half of a total amount of a third sound signal to the left speaker and a second half of the total amount of the third sound signal to the right speaker so that a user hears the same amount from both the left and right speakers of the headphone unit when the middle finger is moved.

2. The method according to claim 1 wherein the method further comprises providing the first sound signal with a first frequency, the second sound signal with a second frequency and the third sound signal with a third frequency so that the first frequency is higher than the second frequency, that is higher than the third frequency.

3. The method according to claim 1 wherein the method further comprises providing the left, middle and right sensors with microphones to register vibrational sound created when the left, middle and right fingers move against the surface.

4. The method according to claim 1 wherein the method further comprises providing the left sensor with a temperature gauge that sends an alarm signal when the left sensor is exposed to a temperature that is below a first freezing temperature, exposing the left finger to a second temperature, the second temperature being below the first freezing temperature, the left sensor sending an alarm signal to the amplifier unit, the amplifier unit sending an alarm sound signal to the left speaker to alert the user of the freezing condition of the left finger.

5. The method according to claim 1 wherein the method further comprises providing the left sensor with a temperature gauge that sends an alarm signal when the left sensor is exposed to a temperature that is above a first burning temperature, exposing the left finger to a second temperature, the second temperature being above the first burning temperature, the left sensor sending an alarm signal to the amplifier unit, the amplifier unit sending an alarm sound signal to the left speaker to alert the user of the burning condition of the left finger.

6. The method according to claim 1 wherein the method further comprises sending a wireless signal to a bone of a cranium of the user.

7. The method according to claim 1 wherein the method further comprises the left sensor sending a wireless activation signal directly to the amplifier unit of the left speaker.

* * * * *